(12) United States Patent
Ghosh et al.

(10) Patent No.: US 8,422,130 B2
(45) Date of Patent: Apr. 16, 2013

(54) PORTABLE MAGNIFYING INSTRUMENT USEFUL FOR COLPOSCOPY

(75) Inventors: Uday Sankar Ghosh, West Bengal (IN); Tapas Gangopadhyay, West Bengal (IN); Munshi Amirul Alam, West Bengal (IN); Sankar Karmakar, West Bengal (IN); Mihir Kumar Banerjee, West Bengal (IN); Gour Chandra Chatterjee, West Bengal (IN)

(73) Assignee: Council of Scientific & Industrial Research, New Delhi (IN)

( * ) Notice: Subject to any disclaimer, the term of this patent is extended or adjusted under 35 U.S.C. 154(b) by 792 days.

(21) Appl. No.: 12/593,589

(22) PCT Filed: Mar. 3, 2008

(86) PCT No.: PCT/IN2008/000118
§ 371 (c)(1),
(2), (4) Date: Sep. 28, 2009

(87) PCT Pub. No.: WO2008/117304
PCT Pub. Date: Oct. 2, 2008

(65) Prior Publication Data
US 2010/0039700 A1  Feb. 18, 2010

(30) Foreign Application Priority Data
Mar. 28, 2007 (IN) .............................. 669/DEL/2007

(51) Int. Cl.
*G02B 23/00* (2006.01)
(52) U.S. Cl.
USPC ...... 359/432; 359/798; 362/249.06; 362/804; 600/168; 600/178; 600/180; 600/223
(58) Field of Classification Search .................. 359/422, 359/425, 432, 798, 802, 803; 362/249.06, 362/249.12, 804; 600/135, 160, 162, 163, 600/167, 168, 178, 180, 184, 220, 221, 223, 600/245, 246, 476
See application file for complete search history.

(56) References Cited

U.S. PATENT DOCUMENTS 3,127,115 A * 3/1964 Yellott et al. ................... 600/167
3,608,998 A * 9/1971 Rinker ........................... 359/432

(Continued)

FOREIGN PATENT DOCUMENTS

| CN | 2188395 Y | 2/1995 |
| DE | 866 716 | 2/1953 |
| FR | 2648920 A3 * | 12/1990 |

OTHER PUBLICATIONS

Sellors, et al., "Illumination, optics, and clinical performance of hand-held magnified visual inspection device (AviScope™): a comparison with colposcopy", J Acquir Immune Defic Syndr, vol. 37, Supplement 3, Oct. 2004.

*Primary Examiner* — Frank Font
(74) *Attorney, Agent, or Firm* — K&L Gates LLP

(57) ABSTRACT

A portable magnifying instrument useful for colposcopy is provided which may include in combination an optical system capable of providing a distortion free clear continuously varying 10× to 15× magnification of a three-dimensional wide object; an integrated energy efficient, low powered and intensity controlled illumination system; a power pack and mounting. The optical system may have an eyepiece lens system and an objective lens system. The illumination system may have a plurality of light emitting diodes (LEDs) connected to the power pack; mounted in such a manner that the angle between the LEDs is maintained with respect to the optical axis of the lens system and that the light beam from the said LEDs impinges on the wide object to be observed at the focus of the said lens system.

4 Claims, 5 Drawing Sheets

U.S. PATENT DOCUMENTS

| | | |
|---|---|---|
| 5,479,293 A | 12/1995 | Reed |
| 5,496,261 A * | 3/1996 | Sander .......................... 600/163 |
| 5,840,013 A * | 11/1998 | Lee et al. ...................... 600/114 |
| 6,217,512 B1 | 4/2001 | Salo et al. |
| 6,277,067 B1 | 8/2001 | Blair |
| 6,496,718 B1 | 12/2002 | Lonky |
| 6,712,761 B2 | 3/2004 | Borodulin et al. |
| 6,896,653 B1 | 5/2005 | Vail, III et al. |
| 8,184,367 B2 * | 5/2012 | Rolland et al. ................ 359/383 |
| 2006/0215406 A1 | 9/2006 | Thrailkill |
| 2008/0045791 A1* | 2/2008 | Gal et al. ...................... 600/116 |
| 2011/0275900 A1* | 11/2011 | Gilhuly et al. ................ 600/162 |

* cited by examiner

PORTABLE MAGNIFYING INSTRUMENT USEFUL FOR COLPOSCOPY

CROSS-REFERENCE TO RELATED APPLICATIONS

This application claims the benefit under 35 U.S.C. §371 of International Patent Application PCT/IN2008/000118 filed Mar. 3, 2008, and also claims the benefit of Indian Patent Application 669/DEL/2007 filed Mar. 28, 2007 in India. The entire disclosures of both applications are incorporated by reference herein.

BACKGROUND

Colposcopes deal with wide three-dimensional objects that are neither telescopic nor microscopic in nature and provide magnifications in the range of 6× to 40×. Conventional instruments are heavy, require special expertise to operate, and are so costly that only hospitals can have and use them. To ensure proper utilization of such costly equipment, colposcopes in hospitals are generally shared among a number of physicians for examination/investigation. Associated delay in examination may lead to delay in diagnosis and adds to the cost and suffering of patients.

Presently mass cervical cancer screening camps are organized by many volunteer organizations with an aim to detect cancer among impoverished people at a very early stage. If pre-cancerous stages can be detected for patients by observing the tissue color/pattern change through a magnified view of cervix, very effective treatment can be provided at a favorable time and at an affordable cost. Traditional colposcopes may, however, not be practical for such applications. For example, big, freestanding colposcopes used in hospitals require considerable setting time for its binocular lens system to be positioned and oriented to aim at the cervix inside the usual speculum. Therefore, such instruments may not be suitable for use in screening a large number of patients in mass cancer detection camps, which may be organized at remote villages cost effectively.

In practice a vaginal speculum is used to make the cervix visible within the vaginal cavity and subsequently diluted acetic acid is applied, which changes the color of cancer affected cervical surface tissue. The cervix and the vaginal cavity are illuminated to observe tissue color change visually. The change in tissue structure is difficult to identify while viewing through naked eye even by the most experienced physicians, unless the disease has reached at an advanced stage. An optically magnified direct view assists the experienced physicians to identify even the pre cancerous changes in the tissue color/pattern and increase the effectiveness of the diagnosis. Better identification of affected locations and capability of picking biopsy samples exactly from that area minimizes the number of biopsy samples to be taken. It enhances the accuracy of the diagnosis also. Optical quality of magnifying instrument reduces the chances of "false positive" visual diagnosis and associated agonies of the patients. Sufferings due to delay in treatment associated with "false negative" diagnosis will also be reduced. With fewer number of biopsy sampling from affected zones as identified; the bleeding, pain and associated complicacy can be avoided.

BRIEF DESCRIPTION OF THE DRAWINGS

FIG. 1 illustrates an isometric view of an example instrument in accordance with an example embodiment of the present invention.

FIG. 2 illustrates viewing of the cervix through an example hand held instrument in accordance with an example embodiment of the present invention using a standard speculum.

FIG. 3 illustrates an exploded view an example hand held instrument in accordance with an example embodiment of the present invention.

FIG. 4 illustrates a sectional representation of an example instrument in accordance with an example embodiment of the present invention showing internal details.

FIG. 5 illustrates an isometric view of an example tripod-mounted instrument in accordance with an example embodiment of the present invention.

FIG. 6 illustrates a view of an example pencil battery powered illumination instrument in accordance with an example embodiment of the present invention.

FIG. 7 represents a 1:1 view of an example compact instrument in a briefcase for anywhere use in accordance with an example embodiment of the present invention.

DETAILED DESCRIPTION OF EXAMPLE EMBODIMENTS

Figure 1:
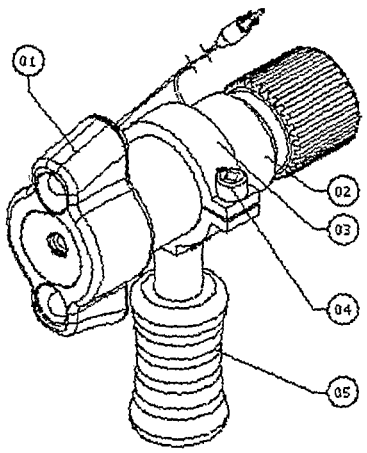
FIGS. 1 to 7 of the drawings accompanying this specification depict example portable magnifying instruments in accordance with example embodiments of the present invention.

Some example embodiments of the present invention relate to a portable magnifying instrument useful for colposcopy. For example, some example embodiments may provide a magnifying instrument for wide objects, such as for the viewing of wide three-dimensional objects inside the body cavity in medical examination by doctors, in particular for observation of the cervix and diagnosis thereafter, e.g. a colposcopic examination. Example portable instruments may magnify an object which is neither situated at a long distance, normally viewed by telescopes, nor at short distance, normally seen through a microscope. Such example embodiments may provide individual medical practitioners with the ability to perform colposcopic examinations anywhere at any time. Example portable magnifying instruments may be useful for screening patients for cervical cancer and may enable very early detection of the disease thus resulting in increased cure and survival rates for those patients.

The statistical accuracy of the process of colposcopy depends on the image clarity while viewing directly through the eyepiece of the big colposcope and repeated examination of the suspected area with continuously varying magnification. In order to achieve similar level of accuracy of big hospital use colposcopes, the portable magnifying instrument should be capable of examining a particular location of the wide object with continuously varying magnification. Some example embodiments of the present invention may provide such a capability. In addition, example embodiments of the present invention may also provide lightweight instruments which may be suitable for hand held use. Example embodiments may also provide for easy changeover to tripod-mountings facilitating the examination of a large number of patients, and the use of low powered LEDs may enhance the usefulness of example embodiments for prolonged use at mass cancer detection camps.

There is a need for a portable instrument capable of producing high quality magnified views of the cervix which individual doctors can use as and when they feel appropriate to example a patient at any place of choice. In addition, there is a need for a hand held, portable magnification device capable of producing a high quality, magnified view of wide objects like the cervix. Accordingly, example embodiments of the present invention may provide a lightweight, handheld, portable, easy to use instrument, which may be optically corrected for aberration and coma like traditional big instruments, which may be capable of distortion free viewing of three-dimensional objects like the cervix, and which may complement the visual information interpretation capability of physicians.

Example embodiments of the present invention may address the requirement of individual gynecologists/obstetricians/oncologists to be equipped with a compact, reliable and easy to use instrument for inspection of the cervix, which may be used after simple training, much as they would use a stethoscope or a blood pressure measuring instrument. The ability to examine patients as and when required at a place of choice of the doctor, reduces the chances of having cancer by identifying the changes in surface tissue pattern at a pre cancerous stage and treating accordingly. Thus for poor patients early detection of cancer will be helpful for effective and quality treatment of the incurable disease at low cost. Easy and prompt detection and treatment of other infections/lesion in the cervix and vaginal cavity will also be possible.

Some example embodiments of the present invention provide a portable magnifying instrument useful for colposcopy.

Some example embodiments of the present invention provide a magnifying instrument for wide objects, which may be used for getting a distortion free clear optically magnified view of the cervix for examining patients at an individual doctor's chamber or in a mass cancer checkup camp, organized at a remote locality for early detection of cervical cancer, with a level of statistical accuracy that is normally achieved with big free-standing hospital use colposcopes, at an affordable price.

Some example embodiments of the present invention may provide individual physicians with a compact instrument having sufficient field of view for observing a wide object so that the whole cervix can be examined by one complete planetary motion of the hand held instrument at a glance.

Some example embodiments of the present invention may provide individual physicians with a portable optical instrument with enough depth of field for observing three-dimensional objects like human organs, so that all points between the farthest and nearest portion of the cervix under observation will be within focus during examination.

Some example embodiments of the present invention may provide individual physicians with a handheld instrument that can produce a continuously varying optically magnified view of the cervix required for screening patients for any change in surface tissue pattern, selecting locations of biopsy, etc., and picking samples exactly from the chosen place to enhance the accuracy of colposcopic diagnosis.

Some example embodiments of the present invention may provide physicians a lightweight optical instrument that may be suitable for prolonged, muscle fatigue free, hand held use during time consuming careful observation of the cervix and biopsy sample collection from desired locations, while allowing full concentration.

Some example embodiments of the present invention may allow users to examine a magnified view of a wide object like the cervix from a close distance, while avoiding either the complexity of dealing with body fluid and artificial lubrication or the obstruction of collecting biopsy samples associated with insertion type of instruments.

Some example embodiments of the present invention may allow users to examine a magnified view of the cervix from a close distance so that disturbances due to vibration of a hand held instrument, and the requirements of high energy, long focus, costly illumination systems can be avoided.

Some example embodiments of the present invention may provide physicians with an optical instrument that may be designed for direct viewing of the cervix looking through a properly designed multi-lens objective and multi-lens eyepiece system for a longer period without straining eyes.

Some example embodiments of the present invention may provide physicians with a simple, easy to use instrument that does not require any costly special training for it's operation and works in conjunction with a standard re-usable speculum, following commonly practiced standard colposcopic examination procedures for early cervical cancer detection, thereby eliminating the possibility of incurring any extra cost of diagnosis.

Some example embodiments of the present invention may provide instruments having continuously controlled illumination capable of providing glare free, optically magnified viewing of wet body tissues like the cervix by varying the light intensity.

Some example embodiments of the present invention may provide a properly focused, overlapping, non-incandescent, multiple source illumination system integrated with the instrument so that three-dimensional wet cervix at a distance inside the speculum can be viewed clearly without causing any heat related discomfort to patient.

Some example embodiments of the present invention may provide a compact, energy efficient illumination capability using a rechargeable standalone energy source for continuous long time anywhere diagnostic use of the instrument.

Some example embodiments of the present invention may provide a compact magnification instrument for wide objects that can be operated using a single hand, allowing the other hand to engage in other necessary activity.

Some example embodiments of the present invention may provide physicians an instrument that they may be able to use for viewing of the cervix for diagnosis wearing the spectacles they are habituated to. Those who may have to use spectacles may be able to use the same instrument without any modification.

Some example embodiments of the present invention may provide physicians an effective instrument which they can afford, while empowering them to fight against the dreadful cervical cancer by detecting the disease even at a pre-cancerous stage and providing low cost diagnosis to patients.

Some example embodiments of the present invention may provide an instrument that can be used off and on by doctors at the bedside of patients in their house at remote villages also for detecting the site of biopsy to be taken.

Some example embodiments of the present invention may reduce the chances of the disease getting overlooked until it starts manifestation due to observation of the cervix through naked the eye by doctors.

Some example embodiments of the present invention may provide a low cost instrument so that the advantages of colposcopic examination and diagnosis processes can reach poor patients to a greater extent and their sufferings can be reduced by providing effective treatment associated with early detection of the disease.

Some example embodiments of the present invention may provide simple compact handheld instruments using a pair of pencil batteries as the self-sufficient power source for an illumination system.

Some example embodiments of the present invention may provide a portable instrument that can provide a properly illuminated, optically magnified view of three-dimensional wide objects of about 10 mm diameter with continuously varying magnification from 10× to 15× when the object is placed at a distance in between 75 mm to 100 mm from the objective lens system and viewed directly through the eyepiece lens system with or without wearing spectacles. Working distance of 75 mm to 100 mm enables the instrument to be used for viewing the cervix from a relatively close range as well as with a low powered illumination source.

In example embodiments, the objective and the eyepiece units may be fixed at the two ends of a light metal tube maintaining the least distance for clear vision. This may be the most important optical requirement for reducing eye strain during examination of the cervix with deep concentration. Single lens objective and eyepiece systems with high magnification may distort the views of a wide object. Moreover due to chromatic aberration with single lenses the image may be blurred. So chemically coated multiple lens objective and eyepiece systems may be used to provide a clear undistorted magnified view of an object, e.g. the cervix. The tube length can be varied continuously by rotating the eyepiece and consequently the magnification may change continuously from 10× to 15× without loosing the view of the cervix being observed.

In example embodiments which allow for hand held use, an aluminum ring may be fitted over the metal tube and a threaded hole may be provided in the ring so that gripping handle can be fitted. The aluminum ring can slide over the tube so that the center of gravity of the instrument can be adjusted to pass through the handle to reduce hand muscle fatigue while the instrument is used for a longer period, e.g. for taking a biopsy exactly from the desired location. Ergonomically designed rubber grips may be provided to help in holding the instrument firmly with sufficient comfort. Using such example instruments, physicians can easily examine the cervix by placing the instrument at a desired position and angle with reference to the speculum and making a planetary motion during hand held use.

The weight of example instruments may be less than half a kilogram. A tripod mounted embodiment of the lightweight instrument on a height adjustable tripod may be used for placing camera for a long exposure, using the same threaded hole of the aluminum ring used for handholding for carrying out a time-consuming detail examination of the cervix. The whole instrument along with the folding camera stand can be carried in a small briefcase to any desired location for observation of a patient's cervix.

Around the objective several light sources, e.g. 1.5V LEDs in series with a reflector placed at an angle required for focusing the light to the wide object may be used to provide necessary illumination to the cervix. Intensity of the light can be controlled as necessary by smoothly rotating the dimmer switch, producing glare free clear view of the cervix. Energy efficient LEDs may enable the illumination system to be used for a longer period as required in a detailed examination or when observing multiple patients in a makeshift mass cervical cancer detection camp. The illumination system may be powered, e.g. by an ordinary 6V sealed battery easily available in the market. In example embodiments, low power lighting sources can provide light for a longer period enabling the physician to examine more patients without recharging as frequently. Low power lighting also generates less heat, thereby reducing associated patient discomfort. Power may be supplied from a compact power supply unit that also contains a battery-charging circuit for repeated charging of the battery from standard, e.g. 240V AC, power supply. All components of the lighting system including LEDs, Battery, Charging circuit etc. are cheap and available in market, so spares will be available in the local market of the user in case of any requirement of parts replacement.

A low powered illumination system using LEDs may allow the use of twin pencil batteries as a power source, allowing the instrument to be used for a considerable time before replacing the batteries. This makes the instrument self-contained, more easy to use, simple and compact. In an example pencil battery powered embodiment, a couple of ordinary low cost 1.5V pencil batteries may be placed in the cavity of the handle, so that the center of gravity of the instrument will pass through the handle to reduce muscle fatigue. Alkaline batteries may increase the time of continuous use and rechargeable Nickel Cadmium batteries may reduce the cost of operation even lower, thereby reducing the cervical cancer investigation cost.

Some example embodiments may provide a portable optical instrument having all the features required for a colposcopic examination with high statistical accuracy. Thus, doctors can examine a glare free magnified image of a wide three-dimensional object like the cervix using the hand held unit and can take biopsy samples from exactly desired location either at their chamber or in a temporarily makeshift medical camp.

Some example embodiments may provide all of the features described herein in a single unit, e.g. portability, light weight, hand held or fixed type use, optical systems specially designed for producing magnified views of wide 3D objects at a distance of about 75 mm with a comfortable depth of focus and sufficient field of view, built-in energy saving illumination unit with intensity controller, etc.

Figure 3:
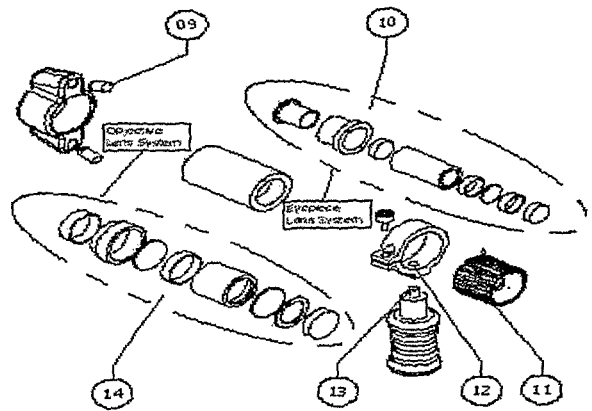
Figure 4:
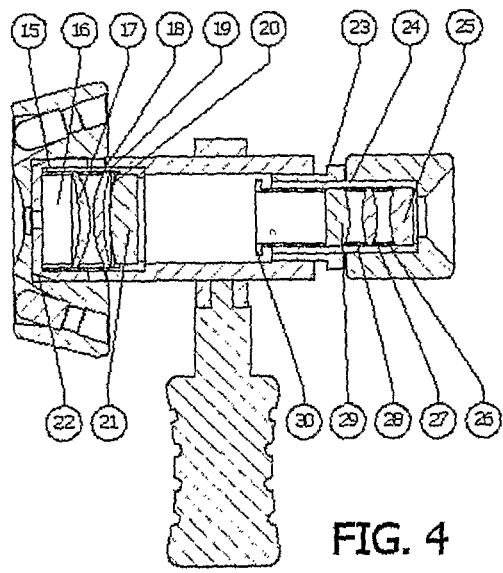

In a handheld example embodiment of the invention as shown in FIG. 1, item no. 1 is the LED holder and item no 2 is the light metal tube of an optical magnification unit for wide objects, which may be attached to the handle 5 via a light metal clamp 3. The position of the magnification unit can be varied to pass the center of gravity of the instrument through the handle to reduce wrist muscle fatigue during prolonged examination of the cervix. Tightening the threaded fastener 4 may tighten the clamp 3 over tube 2. Threaded portion of the handle 13 may be fixed into the threaded hole of the clamp 12 as shown in FIG. 3 and can be removed easily as and when required. FIG. 3 also shows an exploded view of an example optical magnification unit consisting of objective lens system 14 and eyepiece lens system 10 placed at the opposite ends of the light metal tube. Details of objective and eyepiece lens systems are given in FIG. 4. In example embodiments, the objective lens system may have two concavo-convex 17 & 19 and one plano-convex doublet 21. Lights of different colors passing through a thick lens do not converge to the same point on the optical axis and create blurred image. This phenomenon is called chromatic aberration and may be corrected by joining two different types of lens in a structure called achromatic doublet. A coating of suitable material on lens improves the optical quality and reduces chromatic aberration. Spacers 16,18 & 20 of appropriate length may separate optical surfaces of various lenses and all of them along with different lenses are placed within a casing 15. Casing 15 along with all internals is finally placed within aperture 22. Aperture diameter may control the amount of incoming rays and improves the image quality. Eyepiece lens system consists of two coated plano-convex doublets 25 & 29 and one coated double-convex lens 27. Spacers 26 & 28 of appropriate length separate optical surfaces of various lenses and all of them along with different lenses are placed within a casing 24. All internals of eyepiece system may be kept in position by locking them with threaded washer 30. Flange diameter of the threaded washer 30 is bigger than the internal diameter of bronze bush 23 so that the eyepiece system cannot come out of the tube inadvertently when the eye cap 11 in FIG. 3 is rotated for higher magnification. Eye cap 11 and casing 24 are glued together to behave as an integral part and rotation of eye cap actually rotates the whole eyepiece lens system. Rotation of eyepiece system within the bronze bush varies the effective length of magnifier tube, which ultimately varies the magnification of the invention from 10× to 15×. Threaded portion of bronze bush 23 is fixed in the tube 2 by a synthetic anaerobic adhesive called Locktite normally used in jamming threaded fasteners. Outside surface of eye cap 11 may be serrated for better grip to finger and can be rotated effortlessly to vary magnification continuously within the range.

Figure 2:
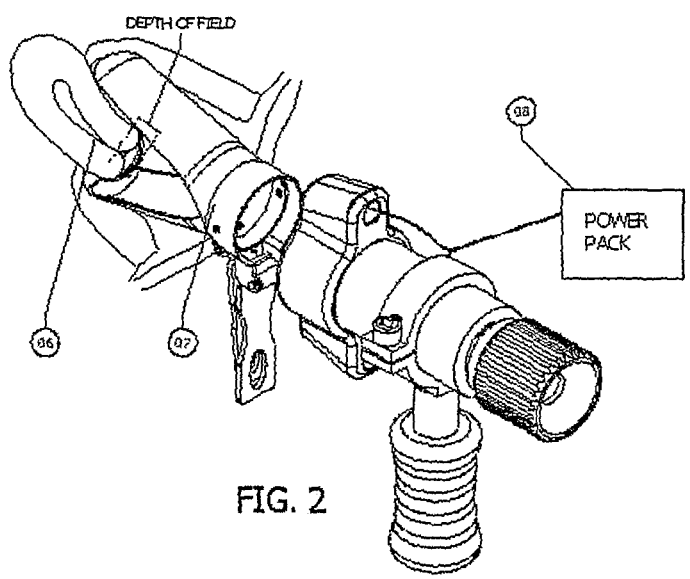

In FIG. 1 item no. 1 is the LED holder which may maintain the angle between the LEDS with respect to the optical axis of the invention in such a way that the light beam from both the LED's are impinging on the wide object at the focal point. Overlapping beams illuminate three-dimensional curved surfaces of cervix to make them visible for examination. Also light reflected from the speculum wall helps in creating an indirectly illuminated environment for the whole cavity. Illumination system is connected to the power pack 8, in FIG. 2 through flexible wire. Two 1.5V LEDs, item number 9 in FIG. 3, may be connected in series and receive 3V DC supply from the power pack. Lights intensity may be controlled from regulator knob 45 in FIG. 7. Power pack may receive power supply from household electric line using plug 46 and charges a standard 6V sealed battery through the charger circuit. Illumination system can be switched off and on by pressing the switch 44 and an LED 43 indicates whether light is on or off.

Figure 5:
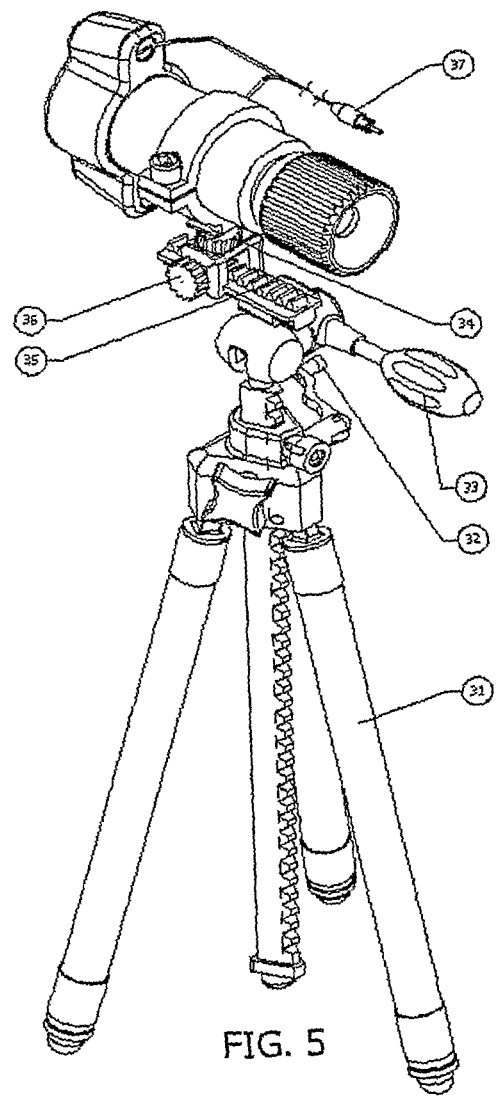
Figure 7:
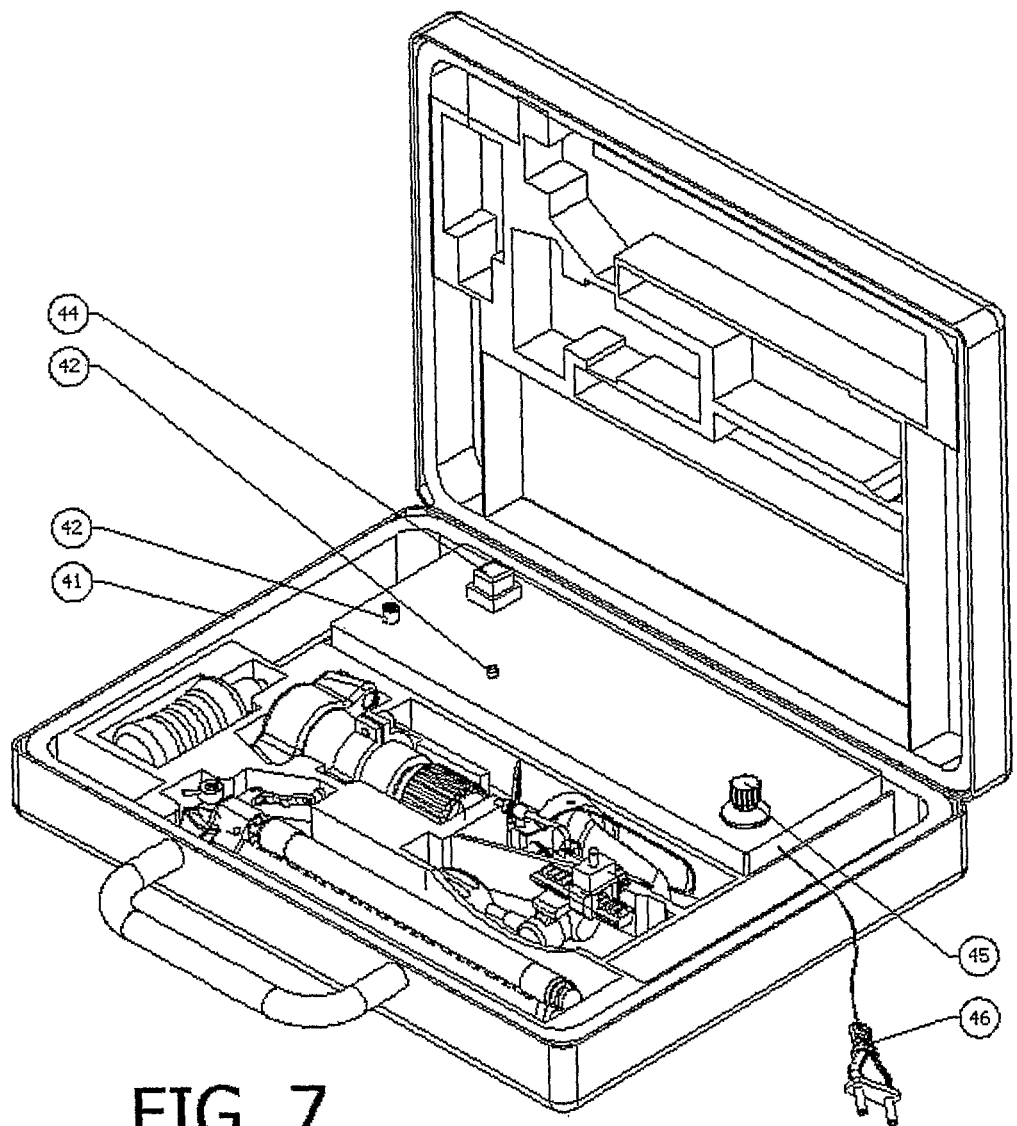

In a tripod-mounted example embodiment of the invention as shown in FIG. 5 item no. 31 is the standard height adjustable camera-mounting tripod used for giving time-consuming long exposure to the film. Invention is fixed to the tripod using threaded screw 34. Rotating handle 32 does fine adjustment in height. Rotating the knob 36 over the rack 35 does fine adjustment along the optical axis. Loosening the knob 33 the instrument can be rotated and inclined to a desired direction. Jack 37 is used to connect the instrument with socket 42 of power pack as shown in FIG. 7.

Figure 6:
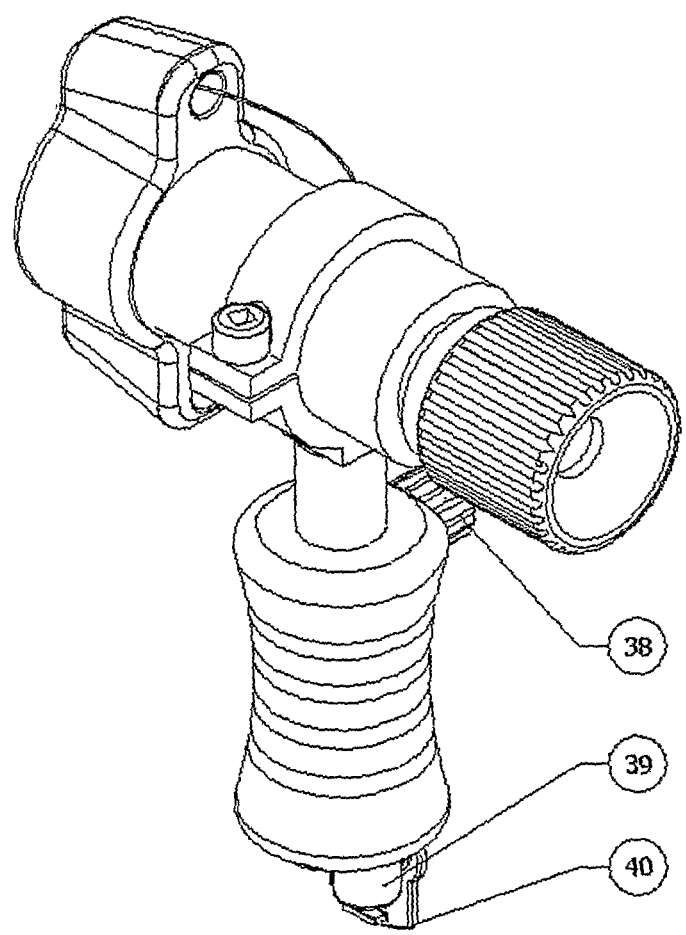

In a pencil battery powered illumination example embodiment of the invention, as shown in FIG. 6, the power supply may be through pencil batteries 39 and the light intensity is regulated by rotating the knob 38 using two fingers, thereby making the system easier to use. Outside surface of the knob is serrated for better grip to finger. End cap 40 is to cover the battery enclosure similar to that found in cameras. or toys.

Portability and compactness may be important. The example in FIG. 7 may be carried easily in a briefcase 41 of size 400 mm×300 mm×80 mm to any location for examination of cervix.

Accordingly, some example embodiments provide a portable magnifying instrument useful for colposcopy, which may include in combination an optical system capable of providing a distortion free clear continuously varying 10× to 15× magnification of a three-dimensional wide object; an integrated energy efficient, low powered and intensity controlled illumination system; a power pack and means for mounting; wherein the said optical system consists of an eyepiece lens system and an objective lens system and the said illumination system consists of a plurality of light emitting diodes (LEDs) connected to the said power pack; duly mounted in such a manner that the angle between the LEDs is maintained with respect to the optical axis of the lens system and that the light beam from the said LEDs impinges on the wide object to be observed at the focus of the said lens system.

In one example, the magnification can be varied continuously by changing the effective tube length by an inbuilt suitable means such as by rotating the threaded eyepiece or translating the eyepiece by a rack-pinion, guide in slot or by other mechanical methods.

In another example, the working distance from the objective lens system is in the range of 75 mm to 150 mm.

In yet another example, the eyepiece lens system may include a combination of multiple lenses including doublets; such as two coated plano-convex doublets with one coated double-convex lens in between.

In still another example, the objective lens system may include a combination of multiple lenses including doublets; such as two concavo-convex and one plano-convex doublet.

In another example, the instrument may include holder such as an ergonomical handle, tripod mounting.

In a yet another example, the intensity controlled illumination system may use a plurality of light emitting diodes (LEDs), e.g., two 1.5V LEDs connected to a power pack such as alkaline, rechargeable battery and being provided with a continuously variable dimmer switch.

A magnifying instrument for wide object which includes an optical system for getting a distortion free clear continuously varying magnified view of three-dimensional wide object like cervix from 10× to 15× when the cervix is viewed directly keeping an eye in the eyepiece, by opening the vaginal passage with a standard speculum and illuminating with the help of integrated energy efficient, low powered and intensity controlled illumination system, by bringing and orienting the portable handheld easy-to-use instrument at a close working distance and with required planetary motion, at any place convenient to the doctors/patients for a colposcopic examination.

In a hand-held example, doctors are to use a standard speculum for opening the vaginal passage and keep cervix visible for examination. Illumination unit of the Invention is switched on and the instrument is brought nearer to the speculum by gripping the handle in one hand. Finer adjustment of the instrument to bring illuminated cervix within focus is done manually by moving it nearer or away from the object while keeping an eye in the eyepiece. Once adjusted the three-dimensional object will be clearly visible as the invention has approximately 5 mm of depth of field, which is sufficient for viewing the curved surface. Due to wide field of view of the invention a considerable portion of the cervix will be visible at a time and the full cervix along with nearby area can be examined with minimum planetary motion of the hand. Viewing of wet body tissue using focused light sometimes produces very bright spot known as glare depending on intensity of the impinged light beam. Doctors can avoid this glare by adjusting the light intensity smoothly using the control knob by the free hand. Biopsy samples can be collected using a biopsy sampler by the free hand from the suspected area identified by seeing the clear, distortion free, direct magnified view of cervix. This helps in detection of cervical cancer well in advance of the stage when the disease can be seen by naked eye and effective treatment at affordable cost can be provided to the patients.

In another example, an instrument may be mounted on a height adjustable tripod normally used in photography for giving long exposure. Folding tripod can be easily carried in the briefcase containing the instrument and can be used for a time-consuming detail examination. The instrument can be tilted and fixed in desired orientation using the tilting and locking mechanism of camera stand and can be positioned on uneven floor by adjusting the tripod legs independently. This makes the use of the instrument feasible at the bedside of the patients in their house at remote location.

In another example, an instrument may contain twin pencil batteries inside the hollow handle to make the system even more compact and a dimmer switch to control light intensity smoothly to produce a glare free distinct view of cervix in hand held condition. Use of two pair of rechargeable pencil batteries, one pair being used in the invention and the other pair being charged using standard battery chargers helps in more effective use of the invention.

Maximum magnification of the instrument may be 15×, but instruments with higher magnification up to 50× can be designed easily by designing new eyepiece and objective lens systems using available optical design software. With increase in magnification field of view decreases, which indicates only a small portion of the object will be visible at a time and more scanning movement will be required for examining the whole cervix. Also with more magnification difficulty in observation due to vibration of hand will become prominent. So a trade off between magnification and field of view is necessary. Working distance of the invention is from 75 mm to 100 mm but instruments with increased working distance up to 150 mm for a close range observation of cervix is possible. Designing of instruments with higher working distance necessitate higher power system to illuminate the wide object inside the speculum cavity and increased heat generation due to more power may cause patient discomfort. Therefore, increasing the working distance needs designing of suitable illumination system.

Weight of the instrument may be less than a kilogram and can be reduced further by use of more synthetic material instead of metal. This will further reduce the chance of hand muscle fatigue.

In order to keep a track of the observations of particular patients doctors may use charts similar to the partitions on a floppy having concentric circles and sectors divided by radial lines. The doctors can mark suspected areas suitably in the chart for future reference during examination. Record of observation in hospital use colposcopes are maintained either by taking photographs of the cervix or by capturing digital images through CCD arrays. Similar arrangements for simultaneous direct viewing of cervix through eyepiece and capturing digital still images for future references can be incorporated into the invention with additional cost without loosing portability.

The example instruments may be particularly for use by individual doctors and various features of the portable light weight handheld instrument is designed in such a way that only one hand of the user will be kept engaged while other hand will remain more or less free for other necessary activity. Activities associated with examination of cervix e.g. removal of vaginal fluid, use of necessary medicines, insertion and picking of 4 samples using biopsy sampler etc. can be done with the free hand. No special training is required and only a simple demonstration of the working of the invention is sufficient for its use as a cost effective portable tool for early diagnosis of dreadful cervical cancer and reducing sufferings of the mankind.

The following examples are given by way of illustration of the working of the invention in actual practice and therefore should not be construed to limit the scope of the present invention.

Example-1

One example instrument has been used for observing various texture of human hand skin at minimum and maximum magnification. Same hand skin texture was observed using a very costly Olympus SZX9 stereomicroscope at 10× and 15× magnifications and the image clarity was compared. It has been found that the image clarity of the present invention is as good as the images produced in the costly microscope.

Example-2

Red color tissue surface inside human mouth normally contains more blood vessels than palm surface and has more resemblance in color with the tissue inside vaginal cavity. So, tissue surface at different places inside oral cavity of a number of people has been observed by smoothly varying the magnification of the invention within the range. Varying the illumination intensity has controlled brightness of the skin surface and glare free undistorted magnified view of the desired locations observed. Performance of the invention in the experiment was quite satisfactory.

Example-3

An experimental health checkup camp was organized in the institute dispensary where gynecologists examined cervix of a number of women and have found that the magnified view of cervix produced by the invention is clear and distortion free. Also it has been observed that the image quality of the portable invention is quite comparable to that of the images produced at hospital use big colposcopes. Moreover the doctors have found the instrument very easy to use, handy and examined one particular location by continuously varying magnification within the range. Depth of focus of the instrument is also found satisfactory. Illumination is sufficient and smooth control of illumination is very effective. No patient discomfort associated to heat generation by illumination had been reported. Doctors felt with the invention as comfortable as other instruments they use regularly for examination of blood pressure, chest etc.

Some advantages of some example embodiments include:
1. Lightweight for hand held use.
2. Portable and compact examination device suitable for outdoor use.
3. Clear distortion free view at close range for direct observation of cervix.
4. Viewing of considerable area at a time and examination of whole cervix with minimum planetary motion.
5. Comfortable depth of field for examination of 3 dimensional wide objects.
6. Capability of continuous variation of magnification within the range.
7. Ergonomic handle for fatigue free prolonged use.
8. Affordable for individual doctors to use the invention in their chamber and in mass cancer detection camps.
9. Can be used for colposcopy at the bed side of patient at remote location.
10. Easy to use and requires no special training.
11. No patient discomfort due to heat generation from light source.
12. Energy efficient illumination system for prolonged at a stretch use.
13. Capability of smooth variation and adjustment of illumination to desired level.
14. Cheaper diagnosis of disease due to low operating cost.
15. Can be used wearing prescription glasses also.
16. Can be used by single hand only keeping other hand free of different work.
17. Ergonomic design of handle for better grip.
18. Highly suitable for time consuming detail examination in tripod mounted embodiment.
19. Minimum eyestrain even with prolonged observation.

20. Very compact in pencil battery powered illumination embodiment.

We claim:

1. A portable magnifying instrument comprising:

an optical system including an eyepiece lens system and an objective lens system, the optical system being configured to provide a continuously variable magnification view of a three-dimensional object;

a controlled illumination system configured to illuminate the object, the illumination system including a plurality of light emitting diodes;

a power supply connected to the illumination system and configured to supply power to the light emitting diodes; and a mounting configured to hold the light emitting diodes so that the angle between the light emitting diodes and the optical axis of the lens system is maintained and so that the light beam from the light emitting diodes can impinge on the object at the focus of the lens system;

wherein the optical system is configured so that the magnification can be varied continuously by changing an effective tube length of the optical system using at least one of a threaded eyepiece, an eyepiece translated by a rack-pinion, or a guide in a slot;

wherein the optical system is configured to provide continuously variable magnification in the range of 10× to 15× magnification and further configured to have a working distance from the objective lens system in the range of from 75 mm to 150 mm;

wherein at least one of the eyepiece lens system or the objective lens system includes a combination of multiple lenses including doublets;

and wherein the illumination system includes two 1.5 v light emitting diodes;

the instrument further comprising:

at least one of an ergonomic handle and a tripod mount coupled to the mounting; and a continuously variable dimmer switch to control the power provided from the power pack to the light emitting diodes.

2. The instrument of claim 1, wherein the eyepiece lens system includes two coated plano-convex doublets and a coated double-convex lens positioned between the two coated plano-convex doublets.

3. The instrument of claim 1, wherein the objective lens system includes two concavo-convex lenses and one plano-convex doublet.

4. A portable magnifying instrument comprising:

an optical system including an eyepiece lens system and an objective lens system, the optical system being configured to provide a continuously variable magnification view of a three-dimensional object;

an illumination system configured to illuminate the object, the illumination system including a plurality of light emitting diodes;

a power supply connected to the illumination system and configured to supply power to the light emitting diodes; and a mounting configured to hold the light emitting diodes so that the angle between the light emitting diodes and the optical axis of the lens system is maintained and so that the light beam from the light emitting diodes can impinge on the object at the focus of the lens system;

wherein the optical system is configured so that the magnification can be varied continuously by changing an effective tube length of the optical system using at least one of a threaded eyepiece, an eyepiece translated by a rack-pinion, or a guide in a slot;

wherein the optical system is configured to provide continuously variable magnification in the range of 10× to 15× magnification and further configured to have a working distance from the objective lens system in the range of from 75 mm to 150 mm;

wherein the eyepiece lens system includes two coated plano-convex doublets and a coated double-convex lens positioned between the two coated plano-convex doublets and the objective lens system includes two concavo-convex lenses and one plano-convex doublet.

* * * * *